(12) United States Patent
Oswald et al.

(10) Patent No.: US 8,784,209 B2
(45) Date of Patent: Jul. 22, 2014

(54) INCREASING USER ENGAGEMENT WITH HEALTH

(75) Inventors: Mark D. Oswald, Medina, WA (US);
Timothy L. Smokoff, Fox Island, WA (US); Joseph M. Sanantonio, Orlando, FL (US); Michael T. Dunn, Orlando, FL (US); Michael K. Reneer, Sanford, FL (US); Vesela Randelov, Orlando, FL (US); Yanli Xia, Oviedo, FL (US); Michael Helmick, Oviedo, FL (US); Linda Z. Massie, Winter Springs, FL (US)

(73) Assignee: Imetrikus, Inc., Seattle, WA (US)

(*) Notice: Subject to any disclaimer, the term of this patent is extended or adjusted under 35 U.S.C. 154(b) by 0 days.

(21) Appl. No.: 13/607,548

(22) Filed: Sep. 7, 2012

(65) Prior Publication Data

US 2013/0090749 A1   Apr. 11, 2013

Related U.S. Application Data

(60) Provisional application No. 61/532,080, filed on Sep. 7, 2011.

(51) Int. Cl.
*G07F 17/32* (2006.01)

(52) U.S. Cl.
USPC ................... 463/39; 463/31; 434/247

(58) Field of Classification Search
USPC ................. 463/39, 31; 434/247
See application file for complete search history.

(56) References Cited

U.S. PATENT DOCUMENTS

| | | | |
|---|---|---|---|
| 7,092,846 B2* | 8/2006 | Vock et al. | 702/182 |
| 2004/0210458 A1 | 10/2004 | Evans et al. | |
| 2009/0076842 A1 | 3/2009 | Schwarzberg et al. | |
| 2009/0076903 A1 | 3/2009 | Schwarzberg et al. | |
| 2010/0228561 A1 | 9/2010 | Boyce et al. | |
| 2010/0292600 A1 | 11/2010 | Dibenedetto et al. | |

OTHER PUBLICATIONS

Patent Cooperation Treaty, International Search Report and Written Opinion, International Patent Application No. PCT/US2012/054319, Nov. 27, 2012, 18 Pages.

* cited by examiner

*Primary Examiner* — Omkar Deodhar
(74) *Attorney, Agent, or Firm* — Fenwick & West LLP

(57) ABSTRACT

A health-program system and method provides health programs for users to select, receives data related to users' progress in a selected health program and determines users' status in the program which is provided for display to the users.

21 Claims, 21 Drawing Sheets

FIG. 7

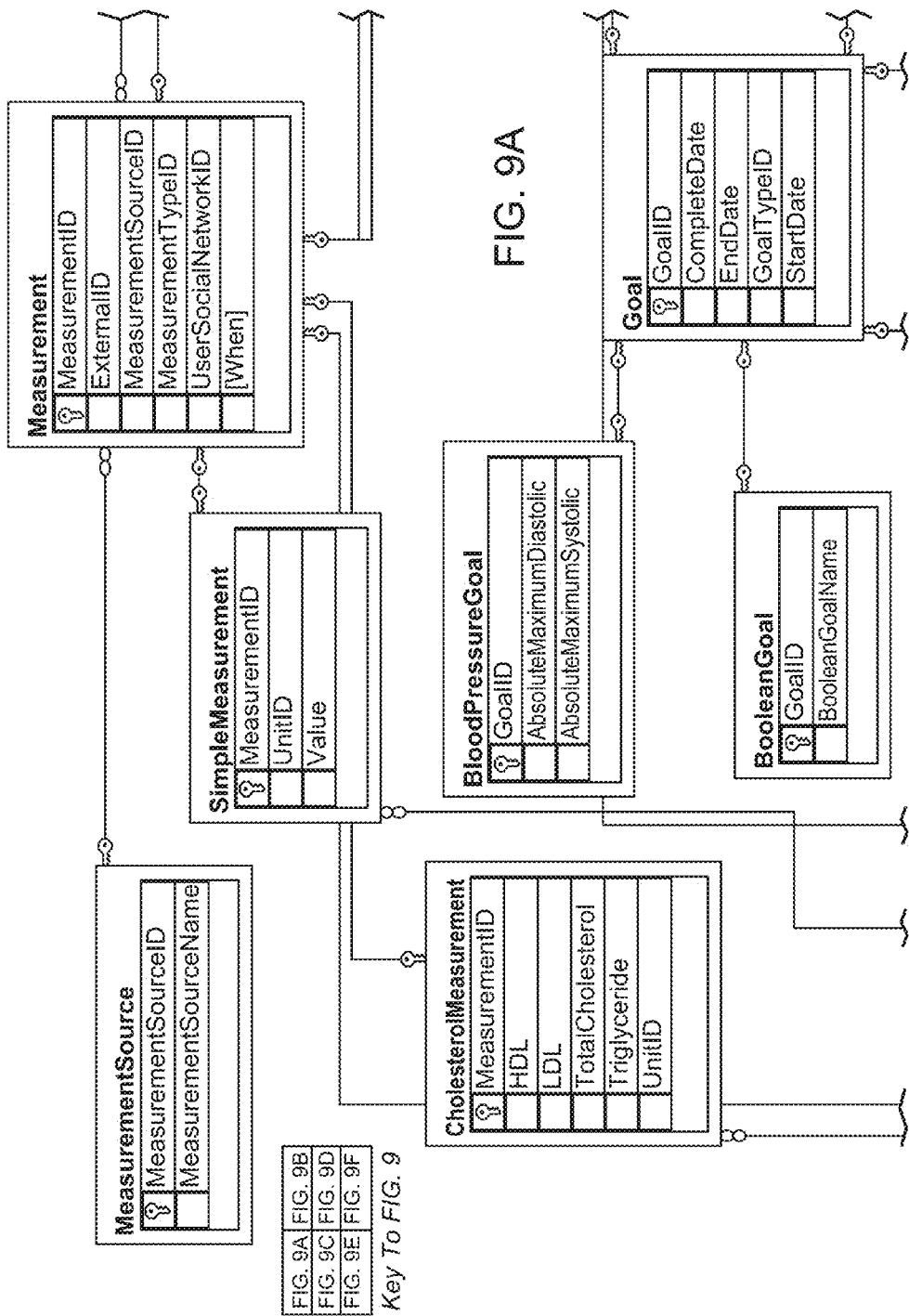

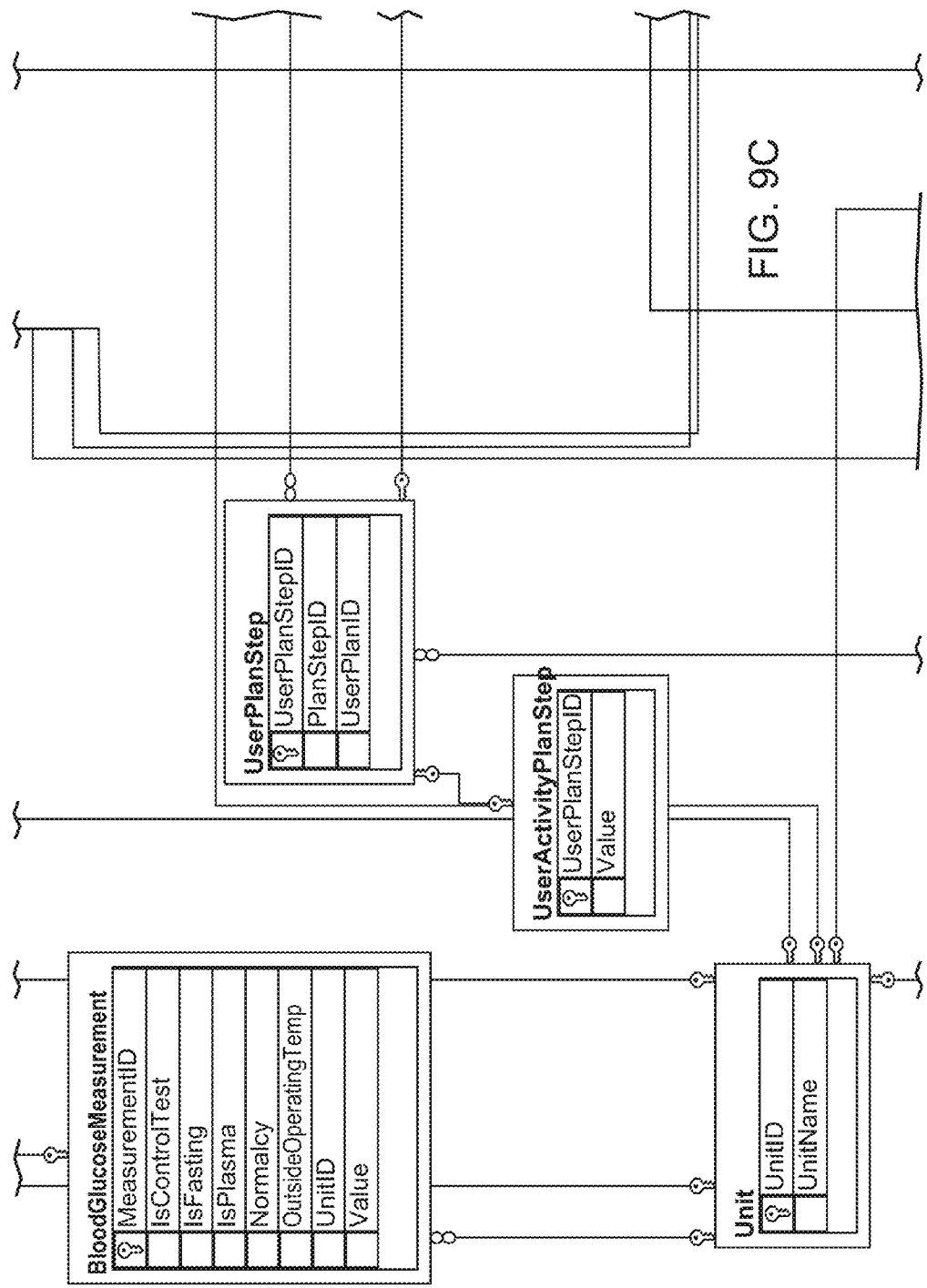

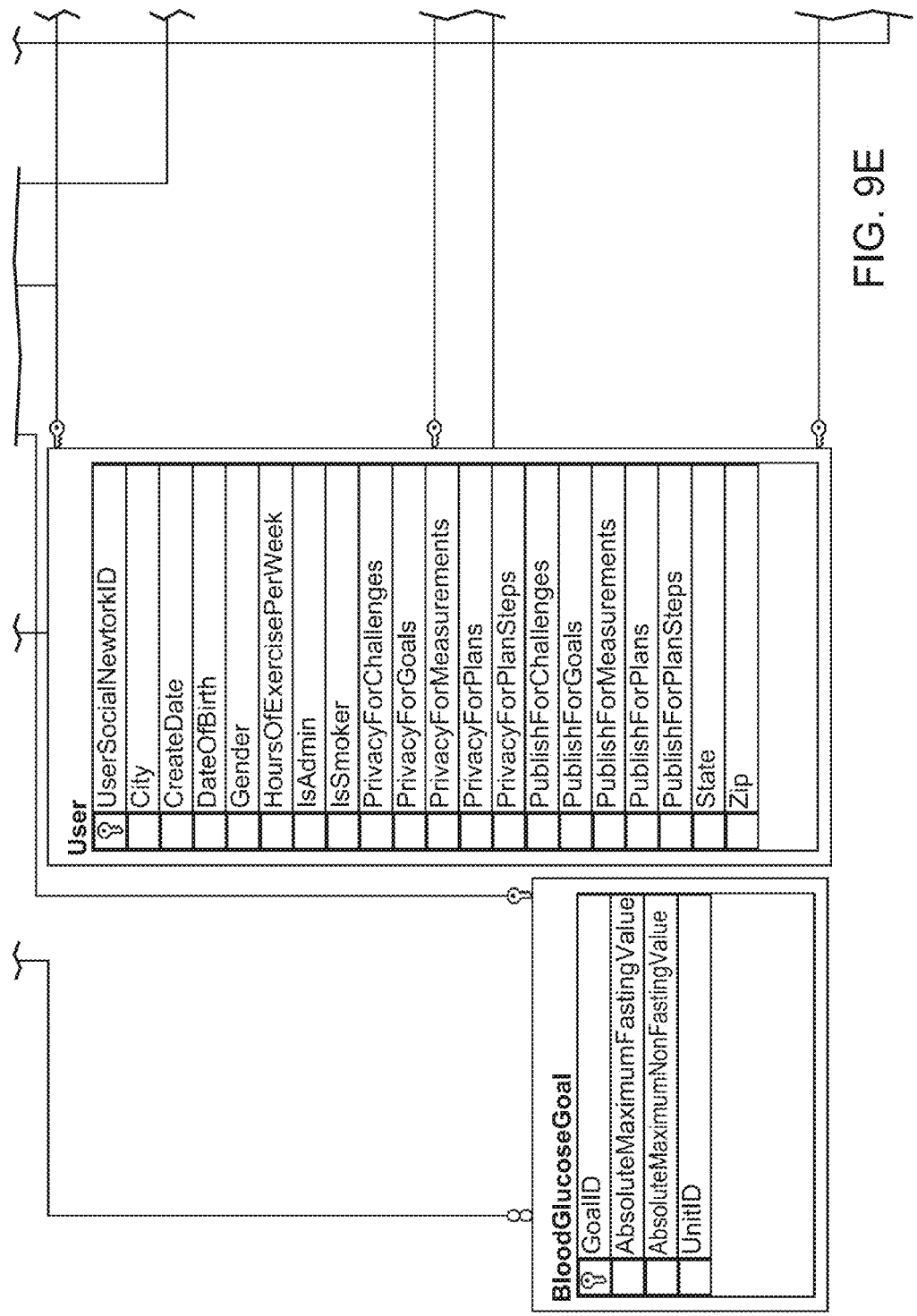

INCREASING USER ENGAGEMENT WITH HEALTH

RELATED APPLICATIONS

This application claims priority to U.S. Provisional Application No. 61/532,080 filed Sep. 7, 2011, which is hereby incorporated by reference in its entirety.

FIELD

The present disclosure relates to on-line applications to increase user engagement with health through participation in activities related to health.

BACKGROUND

Healthcare costs are a major concern for individuals, employers and governments at the local, state, and federal level. A majority of healthcare expenses could be avoided as they are associated with disease and morbidity that could be avoided. Peer pressure, which is often associated with pressure to participate in negative activities, can be a force for good in increasing health. Many people are motivated to make positive health-related changes following the example of friends, family and coworkers. Similarly, when an individual's motivation to stick with a plan, such as a work-out plan, ebbs, often encouragement from others reenergizes the individual. Just knowing that others are counting on you to encourage them can be the difference between sleeping in and getting up to work out on a given morning.

SUMMARY

The described system stores health-related programs to assist users in meeting their health needs. Users browse the programs to select one to join. Users can browse programs or search for on certain criteria. Health related programs include plans and challenges which can take the form of a health related goal or a routine. A plan is designed for use by a user individually and does not require others to participate. A challenge provides a team environment in which multiple individuals participate jointly. Both plans and challenges can be created by individuals or by corporate entities. Status in plans and challenges is determined using data provided either by the user or by health monitoring devices or a combination of the two and displayed to users in dashboards.

BRIEF DESCRIPTION OF THE DRAWINGS

Figure 7:
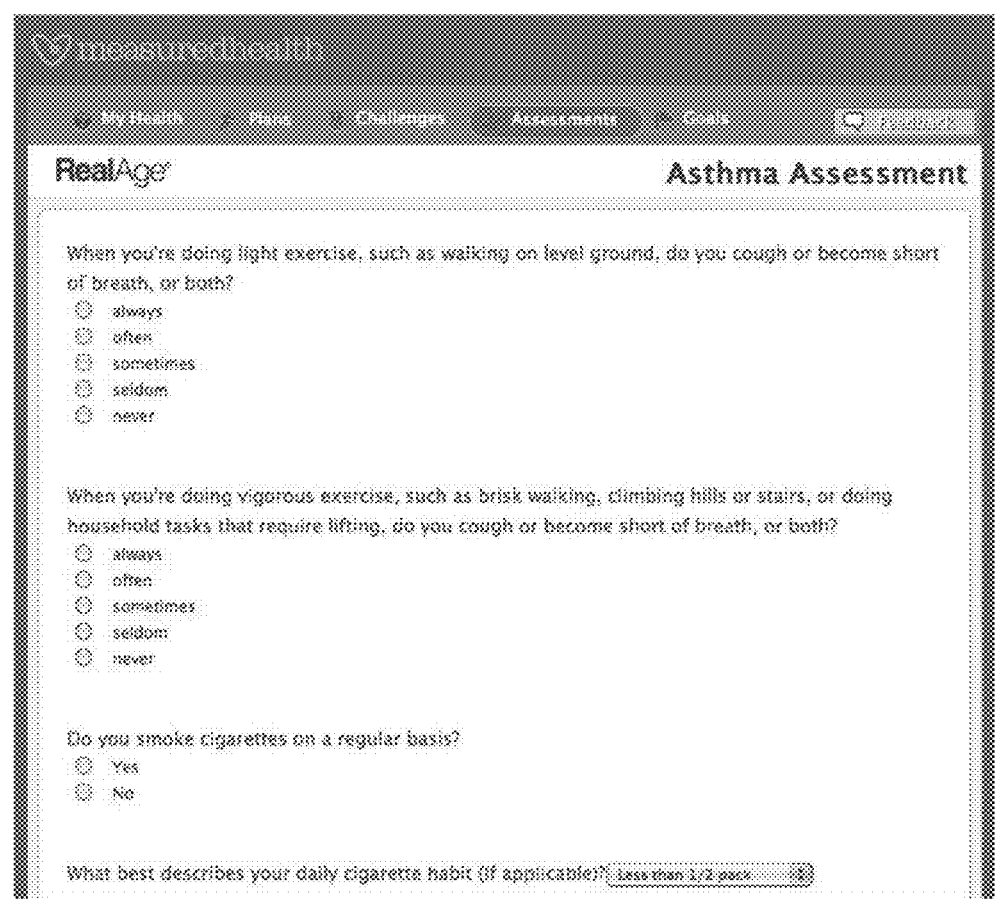

FIG. 7 is a user interface displaying a selected assessment.

The figures depict a preferred embodiment of the present invention for purposes of illustration only. One skilled in the art will readily recognize from the following discussion that alternative embodiments of the structures and methods illustrated herein may be employed without departing from the principles of the invention described herein.

DETAILED DESCRIPTION

General Overview

The described system stores health-related programs to assist users in meeting their health needs. Health related programs include plans and challenges which can take the form of a health related goal or a routine. A plan comprises health related activities, and may include activities related to diet, exercise, fitness, mental health, sports, and the like. Plans are joined by individuals and proceed with or without other users. A challenge provides a team environment in which multiple individuals participate jointly. Both plans and challenges can be created by individuals or by corporate entities. Status in plans and challenges is determined using data provided either by the user or by health monitoring devices or a combination of the two and displayed to users in dashboards. Users choose whether or not to share their participation and data from plans and challenges with friends via one or more online social networking platforms. If the user has opted into sharing, the system posts updates about the user's participation to the social networking platform.

In a challenge, multiple users participate in a goal or routine and one or more prizes are awarded. Challenges may be competitive or cooperative. In a competitive challenge, prizes are awarded only to the first N individuals who complete the routine or achieve the goal, where the value of N is established by the creator of the challenge. In a cooperative challenge, all participants who achieve the goal or complete the routine are awarded a prize.

System Architecture

Figure 1:
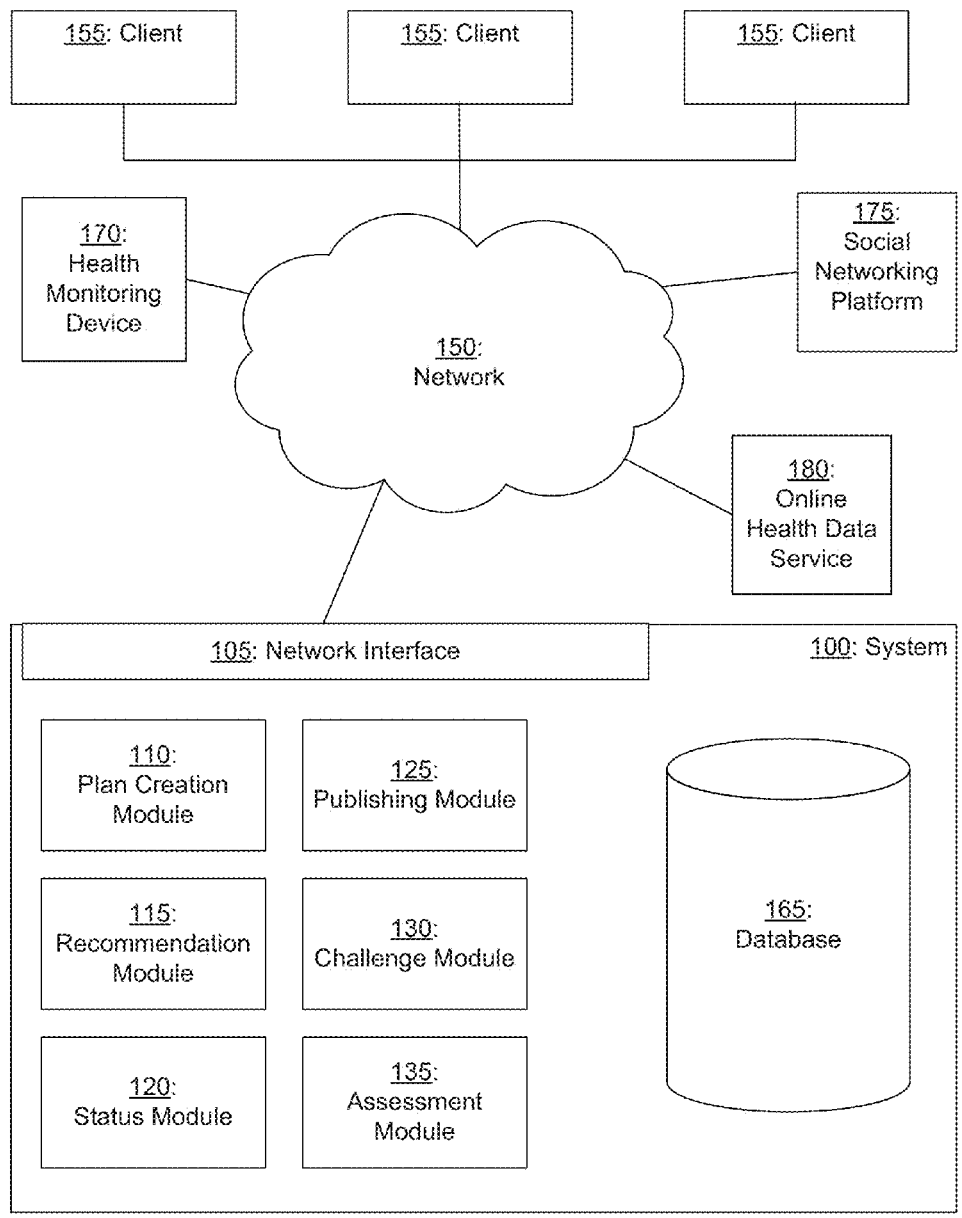
FIG. 1 is block diagram of the architecture of a computer system for implementing one embodiment.

FIG. 1 is a high-level block diagram of the environment for the system 100 according to one embodiment. The system 100 communicates with clients 155, a health monitoring device 170, a social networking platform 175 and an online health data service 180 via the network interface 105 and network 150.

The system 100 is implemented using a computer system comprising a single computer, or a network of computers, including cloud-based computer implementations. As used herein, a "computer" is understood to mean a hardware device including at least one processor, a memory configured for storing computer executable programs and data, a storage device for persistent storage of programs and data, a bus for communicatively coupling the processor(s), memory, storage, and associated physical and programmatic interfaces for input devices, output devices, and network connectivity. Generally, the computers are preferably server class computers including one or more high-performance CPUs and 1G or more of main memory, as well as 500 Gb to 2 Tb of computer readable, persistent storage, and running an operating system such as LINUX or variants thereof. The operations of the system 100 as described herein can be controlled through either hardware or through computer programs installed in the storage and executed by the processors of such servers to perform the functions described herein. The system 100 includes other hardware elements necessary for the operations described here, including network interfaces and protocols, input devices for data entry, and output devices for display, printing, or other presentations of data. As is apparent, the various data processing operations described herein are sufficiently complex and time consuming as to require the operation of a computer system such as the system 100 in order to practice embodiments of the invention. The system may be implemented via a combination of hardware and software, as described, or entirely in hardware elements. Conventional aspects, such as network interfaces (e.g., routers, gateways, firewalls), load balances, security devices, backup devices, and the like, are not shown.

The system 100 includes a plan creation module 110, a recommendation module 115, a status module 120, a publishing module 125, a challenge module 130, an assessment module 135 and a database 165 as described herein. For simplicity only one of each component of the system 100 is shown, but in practice multiples of each may be in operation.

The plan creation module 110 is configured to create plans with information provided by the plan creator, and is one means for performing this function. The operation of the plan creation module 110 is described in greater detail below.

The recommendation module 115 is configured to provide recommended plans to users of the system 100 based on one or more criterion, and is one means for performing this function. The recommendation may be made in response to a search query or provided automatically when a user logs into the system 100. The recommendation module 115 may use output from the assessment module 135 in making recommendations. The operation of the recommendation module 115 is described in greater detail below.

The status module 120 is configured to use data provided by the user and/or by the health monitoring device 170 to determine a user's progress in plans and challenges that the user has joined, and is one means for performing this function. That progress is provided for display to the user at the client 155. A user's status is also stored as associated with that user in the database 165. The operation of the status module 120 is described in greater detail below.

The publishing module 125 is configured to provide information to the social networking platform 175 about a user's progress and participation in plans if the user has opted to share that information, and is one means for performing this function. Providing information can be in the form of posts to the user's profile, posts to a news feed, or creating a status update. Additionally the publishing module 125 processes invitations initiated by the user to friends to participate in a plan, goal or challenge. The operation of the publishing module 125 is described in greater detail below.

The challenge module 130 is configured to create challenges with information provided by the challenge creator, and is one means for performing this function. The challenge module 130 also operates challenges and provides the information for providing status of the challenge participants to the participants. Its operation is described in greater detail below.

The assessment module 135 is configured to provide assessments in which users can participate, and is one means for performing this function. Assessments are a series of questions that users answer, and for which a score is generated after completion of the assessment using a scoring algorithm. The subject of the assessment can be anything of interest to users. Assessments will typically be health-related. Examples include, but are not limited to, assessments for type II diabetes risk, asthma management, biological age, overall happiness and the like. The output of the assessment module 135 is stored in the database 165. Operation of the assessment module 135 is described in greater detail below.

The database 165 is configured to store data related to the system. The data may be stored using any type of data storage system. Data includes the parameters of plans and challenges, user account information, data about a user's progress in a plan and indices of this data. The database 165 and its architecture are described in greater detail below in reference to Appendix A.

The network 150 is typically the Internet, but may also be any network, including but not limited to a LAN, a MAN, a WAN, a mobile, wired or wireless network, telecommunication network, a private network, or a virtual private network, and any combination thereof.

The client 155 is any type of device that is adapted to access the system 100 and optionally, the online health data service 180 over the network 150 and that allows a user to input information which the client 155 in turn transmits to the system 100. Examples include, but are not limited to, personal computing devices including handheld and mobile devices such as tablet computers, laptops, smart phones and the like. For simplicity only three clients 155 are shown; in practice there will be numerous clients 155 communicating with system 100.

The health monitoring device 170 is any kind of device that collects health-related data and is configured to provide the data to the system 100 over the network 150, and optionally to the online health data service 180. Health monitoring devices include, but are not limited to blood glucose monitors, blood pressure monitors, peak flow meters, treadmills, elliptical machines, rowing machines, pedometers, running computers, cycling computers, weight scales and the like. Smart phones can be configured to operate as health monitoring devices 170 as well as clients 155. A smartphone can be configured as a health monitoring device 170 by configuring it to read a bar code or QR code on a fitness machine, or to receive data wirelessly (e.g., via NFC or Bluetooth) from other health monitoring devices 170. For simplicity, only one health monitoring device 170 is shown; in practice there will be numerous health monitoring devices 170 communicating with system 100.

The social networking platform 175 is any kind of on-line application through which users interact. Examples include FACEBOOK™, MYSPACE™, GOOGLE+™, BEBO™ and the like. The system 100 typically accesses the social networking platform 175 through use of an application programming interface (API). In one embodiment, users interact with the system via the social networking platform 175. The system 100 can be configured to communicate with multiple different social networking platforms 175 concurrently.

The online health data service 180 is any kind of on-line application where users can store health data. Examples include NUMERAINET™, webmd.com, HEALTHVAULT™ from Microsoft, as well as websites and other online services created by insurance companies and health providers.

Process Description

The various processes of the system 100 and operation of its particular modules are now described in reference to FIGS. 2-8.

Creation of Plans

Plans include two main types—goals and routines. A goal is a measured result to which a user aspires. Examples of goals include lose 10 pounds, run a marathon, lower cholesterol by 50 points and swim the English Channel. Routines are a series of activities that a user commits to doing. Examples include swim one mile three times a week, eat three kinds of vegetables a day, read one motivational book a month, walk around the block at lunchtime every day, etc. Routines can include multiple activities and be related to particular goals. For example, a routine might be: 1) swim one mile three times a week and 2) lift weights twice a week. A goal might be to swim from Alcatraz Island in the San Francisco Bay and then a related routine would be a training plan to get the user trained to accomplish the swim from Alcatraz.

Plans can be created by individual users or corporate entities. In creating a plan, the plan creator determines the health measures that are collected to determine the progress of a user who has joined the plan and other plan attributes. Other attributes of a plan can include how long the plan will be available; a description of the plan; a category for the plan; keywords to describe the plan (with an optional weighting for each keyword), a difficulty rating for the plan, a popularity rating, and sponsorship information. Creators also determine to whom the plan will be visible using a set of business rules. An individual user may create a plan and only make it visible to the user's friends on the social networking platform 175. A corporate entity creating a plan may make it visible to everyone, for example if the plan involves the use of the entity's products. Alternatively, a corporate entity may make a plan only visible to its members or its fans on the social networking platform 175. In this way, the corporate entity has created special content that is available as a bonus to members or loyal customers.

Selection of Plans

Figure 2:
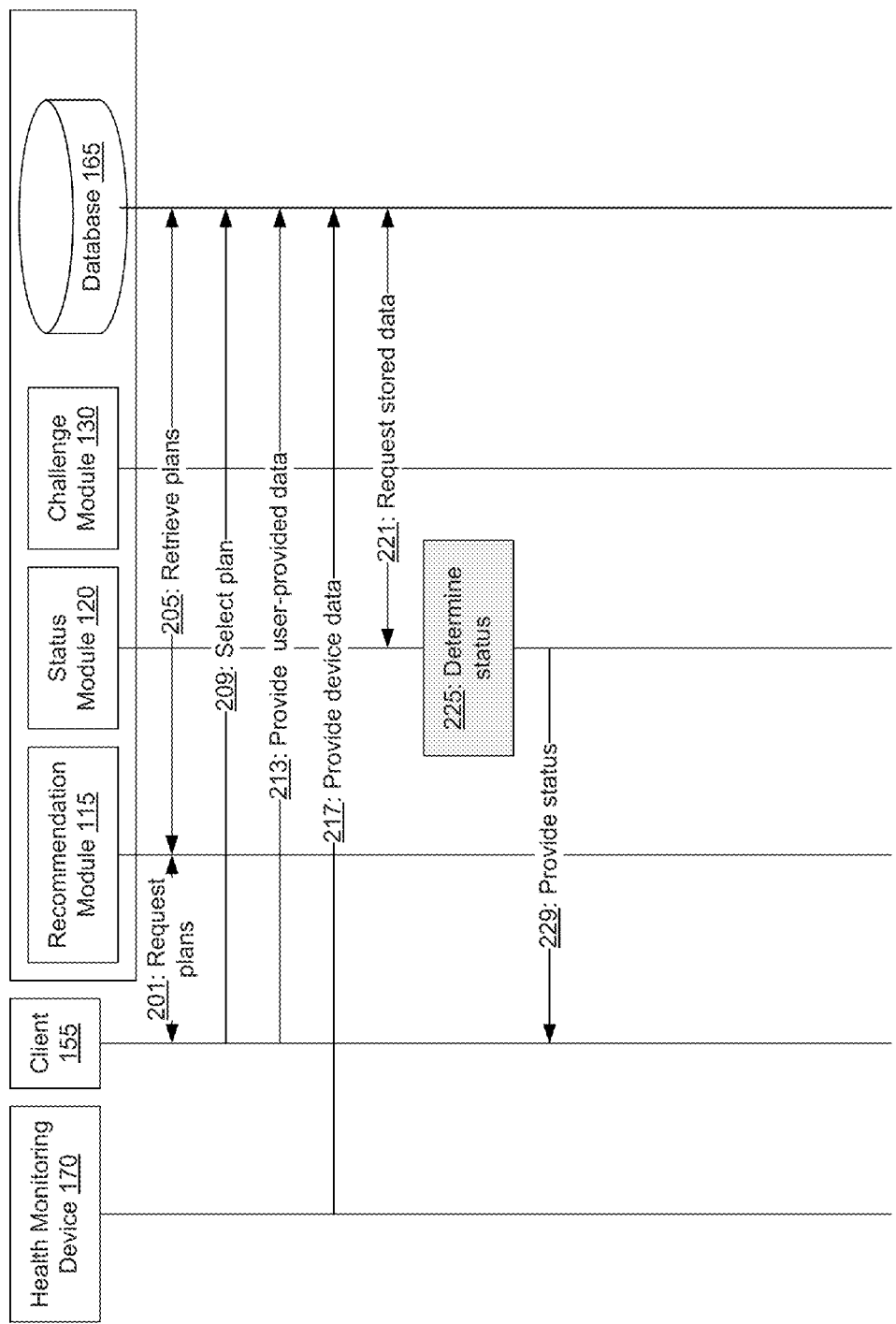
FIG. 2 illustrates the method of selecting a health-related activity and monitoring progress in that activity.

After a user logs into the system 100, the user can select plans to join. Referring to FIG. 2, the user requests 201 plans. In response, the recommendation module 115 provides plans retrieved 205 from the database 165 based on one or more criterion. Provided plans can be plans to browse, plans based on as metadata associated plans such as health condition, activity, plan creator (to view plans created by friends or a particular company or brand), etc. In some embodiments, the system 100 recommends plans to users automatically. When a user sets up an account with the system 100, the user provides a number of items of health data that the recommendation module 115 uses to recommend plans to the user. Examples of data provided to the system 100 include age, weight, whether or not the user smokes, gender, how many hours the user exercises per week, and particular health issues which are of concern to the user (such as type II diabetes, emphysema, obesity, high cholesterol, etc.).

In one embodiment, when recommending plans to a user based on data in the user's account profile, the recommendation module 115 uses the following equation:

$$\text{relevance of plan} = kr*krw + r*rw + rc*rcw + fc*fcw + uc*ucw + pe*pew$$

wherein:

kr=sum of the relevance of matching keywords
  When a plan is created, the creator will have one hundred points to distribute among a variety of keywords. These points represent a level of association or relevance that the keyword has to the plan. Users will be mapped to a set of keywords when using features of the system 100, like taking assessments or joining goals.
  Example:
    Plan A keyword distribution:
      weight loss=80
      reduce stress=5
      make friends=10
      quit smoking=5
    User A keywords:
      quit smoking
      reduce stress
    User A kr=10
r=plan rating=1−(highest rating−plan rating)/highest rating Plans are rated by users. To determine a plan rating, all of the ratings are averaged. In one embodiment, ratings from users are weighted based on information about the user such as, for example, the length of time the user has been a member of the system, how active the user is on the system and the like.

rc=1−(highest rating count of all plans−plan rating count)/highest rating count of all plans fc=friend count=1−(friend count−plan friend count)/friend count uc=plan user count=1−(highest user count of all plans−plan user count)/highest user count of all plans pe=plan efficacy=percentage of users that complete a plan; and Weights (determined through modeling)
  krw=kr weight=0.4
  rw=r weight=0.1
  rcw=rc weight=0.1
  fcw=fc weight=0.1
  ucw=uc weight=0.1
  pew=pe weight=0.2

Figure 3A:
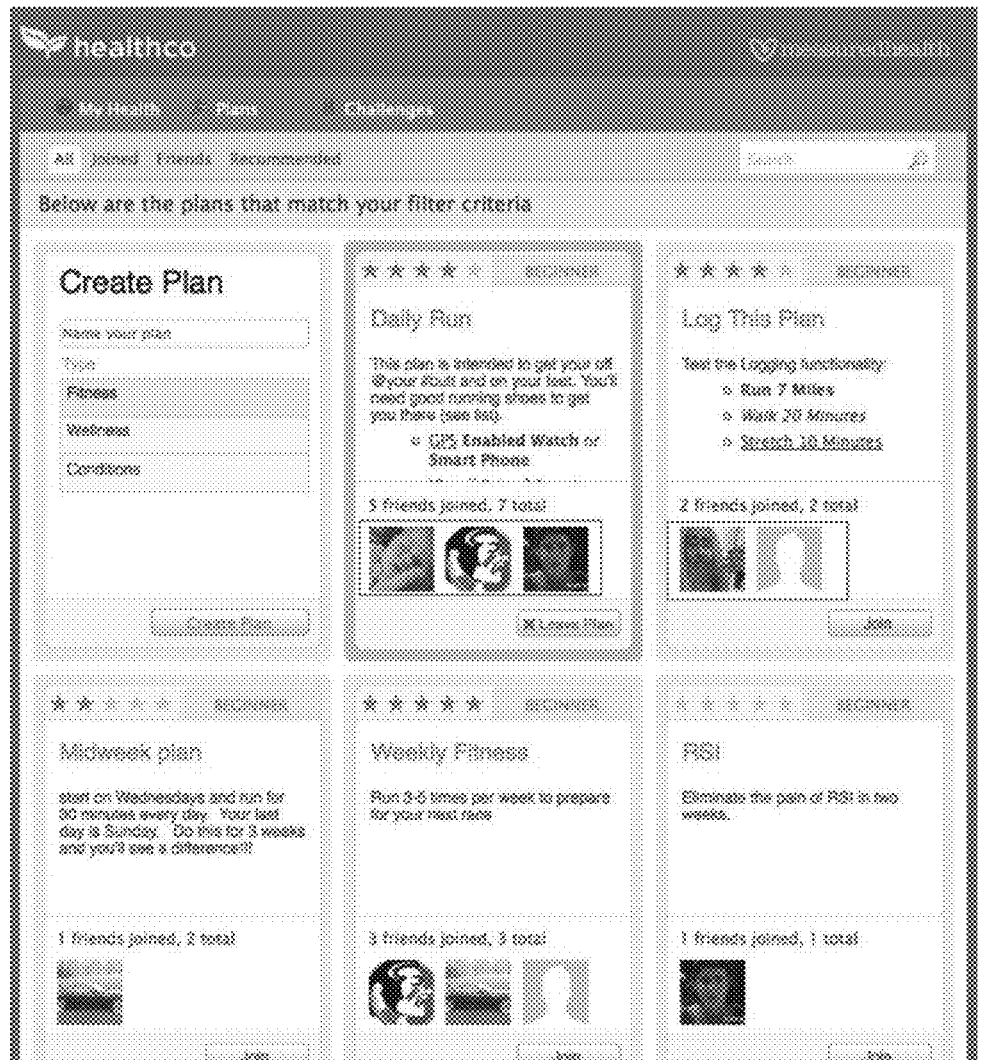
FIGS. 3A-3B are views of a user interface displaying plans to a user.
Figure 3B:

FIG. 3A is an example of plans provided to a user at client 155 by the recommendation module 115. In this example, the recommendation module 115 took into account search criteria, or filters, that the user provided in making a recommendation. There are tabs that allow the user to instead select plans joined by friends or those that are recommended by the recommendation module 115 based on the user's account profile (as described previously). The interface in FIG. 3A also has a tab that allows a user to view all plans that have been joined. FIG. 3B provides a view of plans provided to a user on a mobile device.

The user selects 209 a plan in which to participate and the selected plan is stored as associated with the user in the database 165.

Plan Marketplaces

Marketplaces provide a mechanism for grouping and presenting, by the recommendation module 115, a set of health content (plans or challenges) to end-users. Marketplaces group content using any criteria that may be useful based on administrative or marketing need. Example criteria for grouping include, but are not limited to, a corporate sponsor, a health issue, and plan creator.

Corporate entities can license the system 100 ("licensees") to create a branded marketplace for that corporate sponsor. The licensee selects the specific plans that appear within its marketplace from a library of available plans. Licensees can also create new plans. Like any creator of a plan, a licensee can leverage a set of associated business rules that affect visibility of the created plan. For example, licensee may create a plan that is only visible to its members. A licensee also uses business rules to determine placement of its plans within its marketplace.

Marketplaces are managed from a marketplace administrator user interface, which includes tools that allow for selection from a list of all available content. Using this tool, the administrator for the marketplace selects a specific plan or challenge to preview more detailed information such as plan description, schedule, activities, and ratings. This helps the administrator decide whether to include the plan in the marketplace. Once a plan has been selected, the tool will prompt the administrator to supply additional information that is needed for the associated business rules for the appearance of that plan in that licensee's marketplace. This information includes— start/end dates for content availability, payment/billing related information for premium plans, and also an optional ranking value (numeric) that affects how available plans are sorted within the marketplace display. In one embodiment, the ranking value of plans in a marketplace is determined by factors such as nature of the marketplace (e.g., general, or licensee specific), popularity of the plan, level of difficulty of the plan, cost of the plan, efficacy of the plan (e.g., measured by successful completions of the plan), recency of the plan, and the like.

Status in Plans

Once a user has joined a plan, the system 100 periodically monitors the user's status and provides the status to the user. Status for a goal is the user's progress towards the goal and status for a routine is compliance with the routine.

The status module 120 determines a user's progress towards a goal (f(m)) using data provided to the system 100 and stored in the database 165. From a progress perspective, goals can be complex or simple. A simple goal is one for which progress is tracked using one metric (e.g., weight, waist measurement, etc.).

$$f(m) \text{ for simple goal} = [(m - m_i)/t] \times 100$$

wherein:
m: Current Measurement
Initial Measurement
t: Target Measurement Change (with sign to indicate positive or negative change)
Examples:
Lose 15 pounds: m=160, t=−15, $m_i$=165
f(160)=[(160-165)/−15]×100=~33.34%
Gain 10 pounds: m=155, t=10, $m_i$=150
f(155)=[(155-150)/10]×100=50%

Measurements to determine progress are provided 213 by the user via the client 155 or are provided 217 from the health monitoring device 170. In the examples shown, a weight scale configured to access the network 150 can transmit the data to the system 100 after the user weighs himself. To provide status, the status module 120 requests 221 the stored data to determine 225 the status.

Complex goals require multiple metrics to calculate the desired value. For example, blood pressure has two components—systolic and diastolic. Progress towards a complex goal can be displayed to the user as a history of the measurements over time rather than determining a percentage of progress made towards the goal. Alternatively, more complex progress measuring algorithms can be used that are specific for complex goals, based on a combination of both simple progress as set forth above, and health related factors (e.g., measurements relative to known measurements indicative of good health, such as weights, BMI, HDL, etc.). These are then used to calculate percentage of progress towards the goal.

Compliance with a routine, f(t), is determined by the status module 120 also using data provided by the user to the system 100 (or provided by a health monitoring device 170). The status module 120 uses an "activity weighting" system that the creator of a routine uses to indicate the level of importance for each activity in the routine. The activity weighting is a 0-5 value of increasing importance (where a 0-weighted activity is not factored into routine compliance and a 5-weighted activity is assigned the highest relative importance). On this scale, a 3-weighted activity is considered three times more important than a 1-weighted activity. In one embodiment, partial completion of measurable activities is included into the compliance. For example, if an activity specifies that 5 miles should be run, but the user runs only 4 miles, then a pre-weighted activity compliance of 80% will be used in the calculation. Alternatively, having completed more than half of the activity counts as completed and less than half does not count as completed.

An equation for determining, f(t) is:

$$f(t) = \frac{\left(\sum_{n=1}^{t}\left[\text{Max}\left(\left(\frac{a_n \text{ Actual}}{a_n \text{ Target}}\right), 1\right) \times a_n \text{ Weighting}\right]\right)}{\left(\sum_{n=1}^{t} a_n \text{ Weighting}\right)} \times 100$$

wherein:
t: total # of activities from start date to current date
$a_n$: the current activity in the series
Actual: the actual value entered for a measurable activity (non-measurable activities have a value of 1)
Target: the target value for a measurable activity (non-measurable activities have a value of 1)
Weighting: the relative weighting (0-5) of the activity
Example:
On day 5 of a 30 Day plan, one activity on each of the first five days as follows:
Day 1: run 3 miles (weighting: 3): User completed 2 miles
Day 2: Drink 4 glasses of water (weighting: 0): User drank 4 glasses
Day 3: Walk 20 minutes (weighting: 1): User walked 20 minutes
Day 4: Take a walk around the block (weighting: 1): User completed activity
Day 5: Run 5 miles (weighting: 4): User completed 5 miles $$f(t) = [((2/3) \times 3) + ((4/4) \times 0) + ((20/20) \times 1) +$$
$$((1/1) \times 1) + ((5/5) \times 4)]/[3 + 0 + 1 + 1 + 4]$$
$$= 8/9 \times 100$$
$$= 88.89\%$$

The determined status is provided 229 to the client 155. There it may be displayed to the user at a dashboard displayed at the client 155. A user has a main dashboard showing high-level status for each plan and challenge in which the user is participating. Then a more detailed dashboard can be accessed for each plan or challenge that gives additional detail for that plan or challenge. How status for challenges is determined is discussed in greater detail below.

Verified Data

Data received at the system 100 that is verified is more valuable in providing a true picture of a participant's progress in plan or goal. Data that is verified is identified as such in the database 165. When it comes to health, people often slant information they give to be more positive—such as exaggerating how many days they actually work out, minimizing how many times a week they eat fast food, etc. Additionally, there is the possibility for innocent errors. Verified data is not subject to these problems. Examples of verified data include data reported by a health monitoring device 170 or verified by a witness (a friend confirming that a participant spent 30 minutes walking at lunch). It is anticipated that more and more devices will be able to communicate with the system 100 using standard formats (such as HL7 administered by Health Level Seven, a standard setting body for healthcare informatics). Blood glucose monitoring devices at a participant's home can report data back to the system 100. Exercise machines can either report directly to the system 100 how long a participant worked out on the machine or a participant can scan a QR code on the machine with a smart phone as they start working out and when they finish. The smart phone then reports the amount of time spent and the type of machine to the system 100. In yet another alternative, the machine generates a QR code specific to the participant's workout session (such as calories burned, distance gone on machine, etc.) at the end of the session, which QR is then scanned by the user's smart phone and transmitted back to the system 100. This embodiment provides more data to the system 100 but does not require the exercise machine to have a connection to a network. In yet another option, the location functionality on a smart phone (for example by GPS, or network localization, or cell phone tower triangulation) can be used to provide verified data. That the participant was present at the gym, for example, can be used as verification that the user worked out.

The ability to use verified data provides advantages to users and creators of plans and challenges because verified data is more reliable. Creators of challenges can provide additional incentives, beyond the prizes for winning or completing a challenge, for participants to provide verified data. Additionally or alternatively, verified data is given more weight in an algorithm used to determine the winner of a competitive challenge. Scoring of challenges is discussed in greater detail below. In one embodiment, verified data is identified as such at the user's dashboard. If the user has made progress and data visible to friends at the social networking platform 175, providing verified data and having it identified provides the added incentive of bragging rights.

Challenges

Challenges, administered by the challenge module 130, are routines and goals that have a set start and end time and provide a social element by allowing participating users to interact with one other while working on a routine or goal. This provides additional motivation to complete the routine or goal. The attributes of routines and goals that are challenges are the same as attributes for routines and goals that are plans. The routine or goal in a challenge can also be available as a plan but need not be. Like plans, challenges can be created either by individual users or corporate entities who determine the attributes for the challenge.

A challenge involves the awarding of one or more prizes. Prizes can be anything that users might value. Examples of prizes offered by corporate entities might include discount codes for the entity's merchandise or services or free merchandise or services. Where an individual sets up a challenge, the individual can offer more personal prizes such as a donation to the winner's charity of choice, a home-cooked dinner, or a hosted event. Anti-prizes may also be awarded to the losers. An example anti-prize is to be labeled a rotten egg and a humorous icon is next to that participant's name, as their profile picture or as a badge on their profile picture for some period of time after the close of the challenge.

Challenges can be competitive or cooperative. The creator of a challenge determines whether the challenge will be competitive or cooperative. In a competitive challenge, only the first participant (or first N participants) to achieve the goal or complete the routine wins a prize. An anti-prize can be awarded to the participant who finishes last or does not finish at all. In a cooperative challenge, every participant who completes the routine or achieves the goal wins a prize. An anti-prize could still be awarded if participants in the cooperative challenge do not finish at all.

Figure 4:
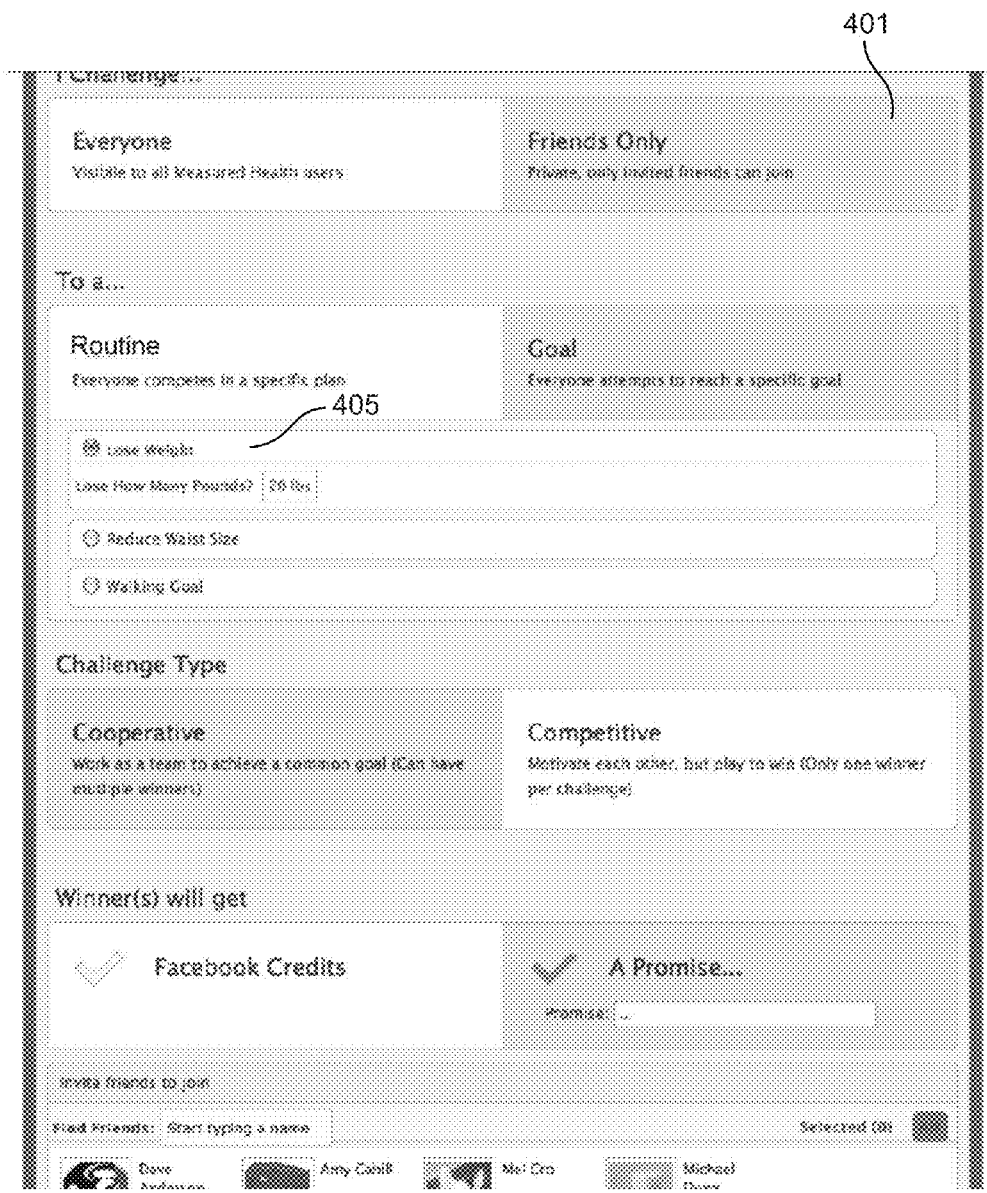
FIG. 4 is a user interface for creating a challenge according to one embodiment.

FIG. 4 is a screenshot of a user interface for creating a challenge. As seen at box 401, the creator of the challenge has challenged friends (as opposed to all users of the system 100) to join in a challenge for a goal to lose 20 pounds and has made it a cooperative challenge. The creator is entering a promise as the prize for all those who reach the goal. Example promises include hosting a party for all who finish the challenge, buying a round of drinks for all finishers, etc.

Users can join a challenge any time before it starts and any time before it ends, i.e. a user can join a challenge that is in progress. Users who have joined a challenge are called participants in the challenge. Participants can leave the challenge any time before the challenge ends. When a participant leaves a challenge, that user is no longer a participant; however, the user can join the challenge again as a participant as long as it has not already ended.

In one embodiment, the data about a participant's progress in the challenge is available to other participants in the challenge. FIG. 4 provides an example dashboard showing the progress of participants in a challenge. The example challenge is sponsored by a corporate entity, "healthco." The prize is a free lunch at a local restaurant. The dashboard displayed to the participant of the challenge includes a button to invite other friends to participate in the challenge. Those invitations are processed through the social networking platform 175.

This challenge is competitive and thus the dashboard includes a leaderboard. For each participant in a particular challenge, the challenge module 130 generates a number, f(p), that represents the participant's progress in the challenge using the algorithm assigned to that challenge. f(p) is nonnegative; the higher the number, the better that participant is doing in the challenge. Participants are ranked in descending f(p) order. If two participants have the same value for f(p), then the participants have the same rank. In one embodiment, the ranking is not dense: e.g., if there are three participants, and two are tied for first, then the last participant is in third place; none of the participants are in second place in this case.

The determination of f(p) depends on whether the challenge is based on a goal or a routine. As discussed in reference to plans, progress is determined differently for goals and routines. For a routine-based challenge, f(p) is a function of compliance with the routine.

f(p)=# compliant activities that the participant, p, has completed wherein a completed activity is compliant if the participant meets the measurement, if any, associated with the activity. If there are no measurements associated with the activity, then the step is compliant by virtue of its being completed.

In an alternative embodiment, participants are ranked based on their compliance with the routine, f(t), as determined by the status module 120 and described previously.

The determination of f(p) for a goal-based challenge to lose weight would be:

$$f(p)=(s(p)-c(p))/(s(p)-n)$$

wherein:
s(p) is the participant's starting weight
c(p) is the participant's current weight
n is the number of pounds to lose. This is specified as part of the challenge and is common to all participants in the challenge.

For a goal-based challenge to reach a certain absolute measurement (e.g., walk 5,000,000 steps), f(p) is just the number of steps each participant has taken to date.

In an alternative embodiment, the challenge module 130 ranks participants based on their progress towards the goal, f(m), as determined by the status module 120 and was described earlier.

Assessments

Figure 5:
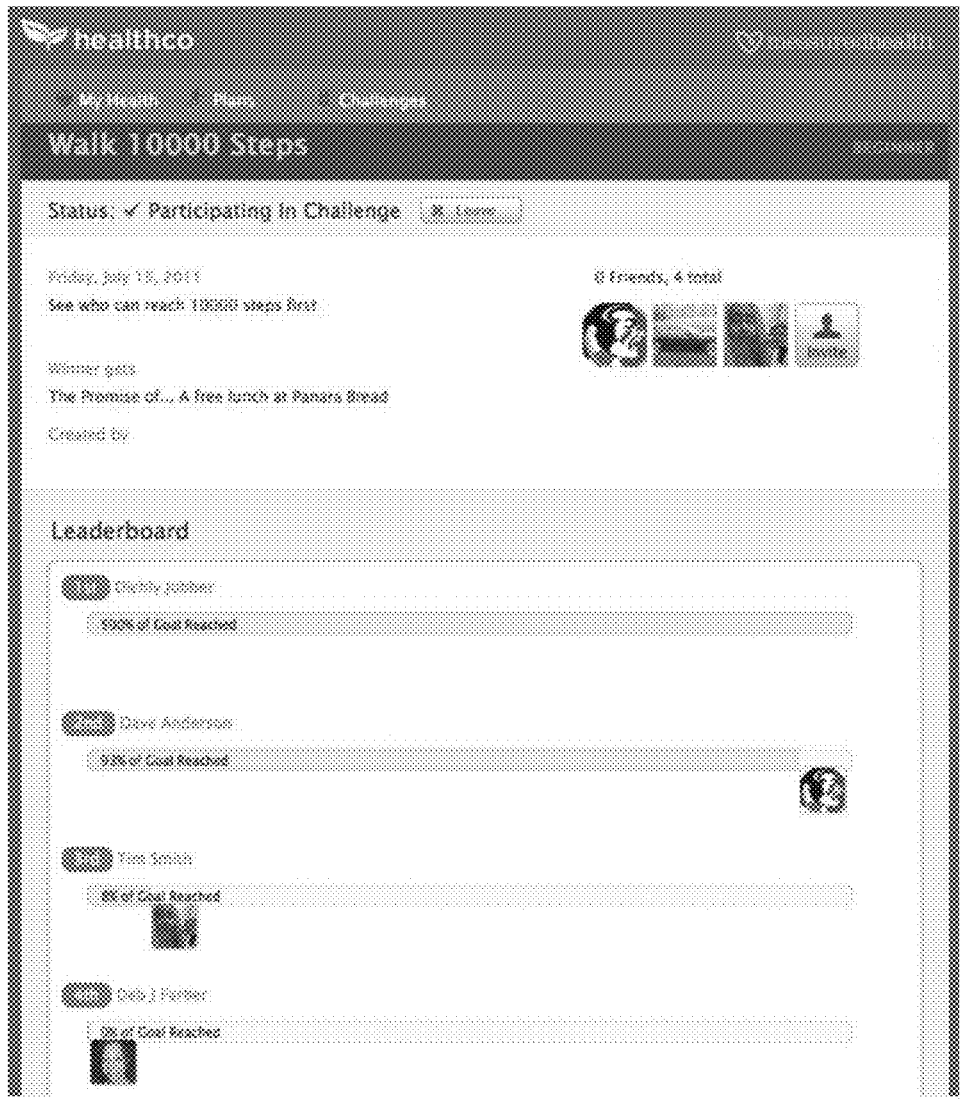
FIG. 5 is a user interface displaying the progress of participants in a challenge according to one embodiment.

In addition to joining plans and challenges, the users of system 100 can take assessments, administered by the assessment module 135. FIG. 5 illustrates a dialog box showing assessments available for a user to take. Assessments 501 can be provided by a third party (e.g., REALAGE™, in this example). Additionally, assessments 505 specific provided by system 100 are presented as well. Assessment 505 is a health survey that asks additional questions beyond those asked in the initial user account set up. If a user has completed assessment 505, the recommendation module 115 uses results of that assessment 505 in recommending plans and challenges to that user. The recommendation module 115 optionally uses the fact that a user has taken any assessment, regardless of the assessment's creator, and its results in making a recommendation for plans and challenges.

Figure 6:
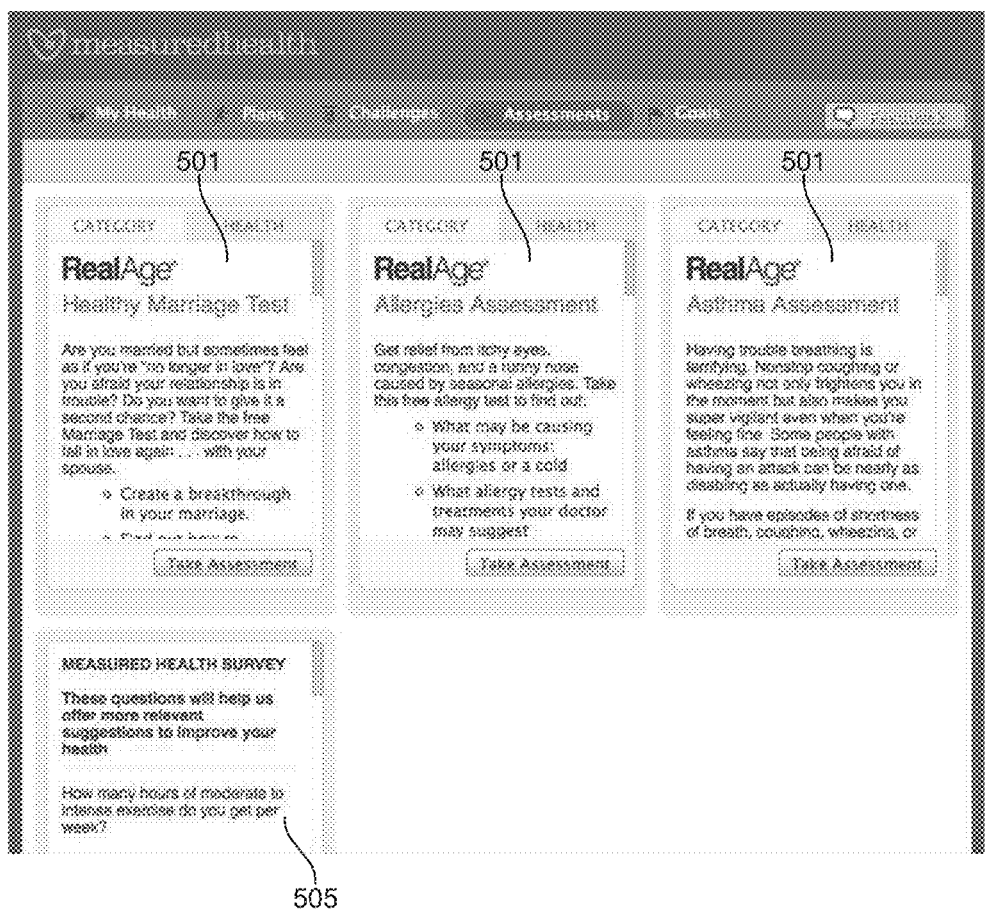
FIG. 6 is a user interface for selecting an assessment.
Figure 8A:
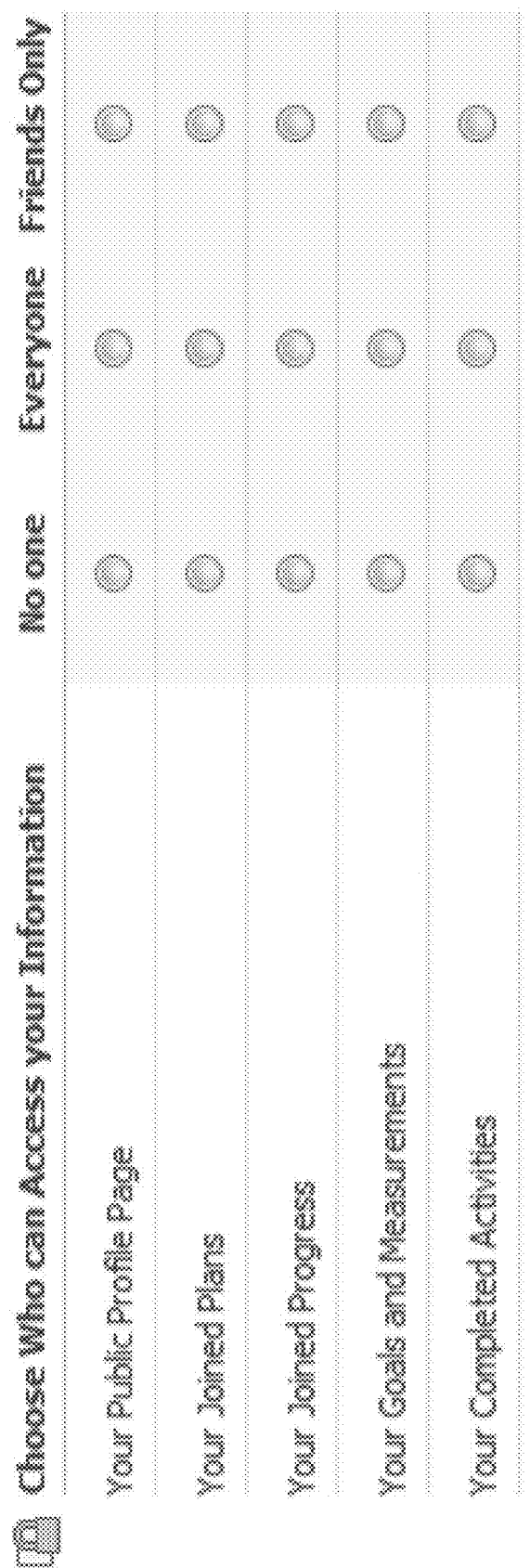
FIGS. 8A-8B are views of a user interface for a user to choose privacy settings.
Figure 8B:

FIG. 6 illustrates the user interface for an asthma assessment. A user's answers are provided to the assessment module 135 which determines a score for the user based on the answers. That score, and optionally the user's individual answers, are stored as associated with the user in the database 165.

Privacy

Privacy is of great concern to users of health-related applications. Users of the system 100 determine privacy settings for each of the different aspects of their participation in the system 100 and then for each of those aspects that the user has decided may be visible to others, to whom will they be visible. FIG. 7A illustrates a privacy control dialog box where the user indicates for each aspect (profile page, joined plans, progress for joined plans, goals and measurements and completed activities) of their participation with the system 100, who, if anyone, can view that aspect. Thus a user can determine whether dashboards of the user's status in various plans can be viewed by friends at the social networking platform 175, by everyone at the social networking platform 175 or by no one. Even if the dashboard is made visible to some people, the user can choose that the individual measurements (blood pressure, steps walked in a day, etc.) will not be visible to others.

In the example in FIG. 7A, the level of control has three options—either no one, everyone or friends only. In other embodiments, additional granularity is implemented such that a user specifies individuals who may view something or can exclude individuals from seeing something. For example, joined plans can be viewed by "Friends Only" except friends John Doe, Mary Jones and Betty Smith. In one embodiment, visibility can further be limited to those at the social networking platform 175 who are also users of system 100. For example, a user could choose to allow all friends at social networking platform 175 or just friends at social networking platform 175 who use system 100 to see a particular aspect. Similarly, visibility could be everyone at social networking platform 175 or everyone at social networking platform 175 who is also a user of system 100. In one embodiment, the privacy options displayed by system 100 are those of the social networking platform 175. FIG. 7B illustrates an alternate interface for making privacy choice, for example for use on a smart phone.

A user's privacy choices are stored at the database 165. In one embodiment, enforcement of the privacy policy is by the social networking platform 175.

In one embodiment, as part of joining a challenge, the user opts to allow the other participants in the challenge to see the user's progress. If a user does not wish to allow that level of access, the user cannot join the challenge. As the purpose of the challenge is to compete, keeping one's progress a secret is not compatible with the spirit of the challenge. The user could of course still participate in the underlying routine or goal that is part of the challenge if that routine or goal is available as a plan. The user would not however be part of the challenge.

Integration With Online Health Data Service 180

Users have the option to have their data from participation in plans provided to an online health data service 180 with whom the user has an account. Additionally, data from health monitoring devices 170 may already be provided to an online health data service 180 and the user can configure their account with the system 100 to retrieve those measurements from the online health data service 180. This avoids having to configure the health monitoring device 170 to provide the data both to the online health data service 180 and the system 100. A user may choose to share other data stored at the online health data service 180 with the system 100. This additional data would allow the recommendation module 115 to provide more personalized recommendations for plans to the user.

Data Architecture

FIGS. 9-13 provide data architecture for storing all of the system 100's data in the database 165 according to one embodiment. In all of the diagrams, a data record including the attributes are shown and the attribute on which the record is keyed. Lines connect records that are keyed to the same attribute (indicated by lines starting and ending in a key icon) as well as connecting records where one record is keyed on the attribute and the other includes the attribute but is not keyed on that attribute (the key end of the line is attached to the data which is keyed on an attribute and then ends with an infinity loop at data that includes that attribute but which is not keyed on that attribute). Please note that throughout FIGS. 9-13, the word "plan" refers to the "routine" type of plan.

Figure 9B:
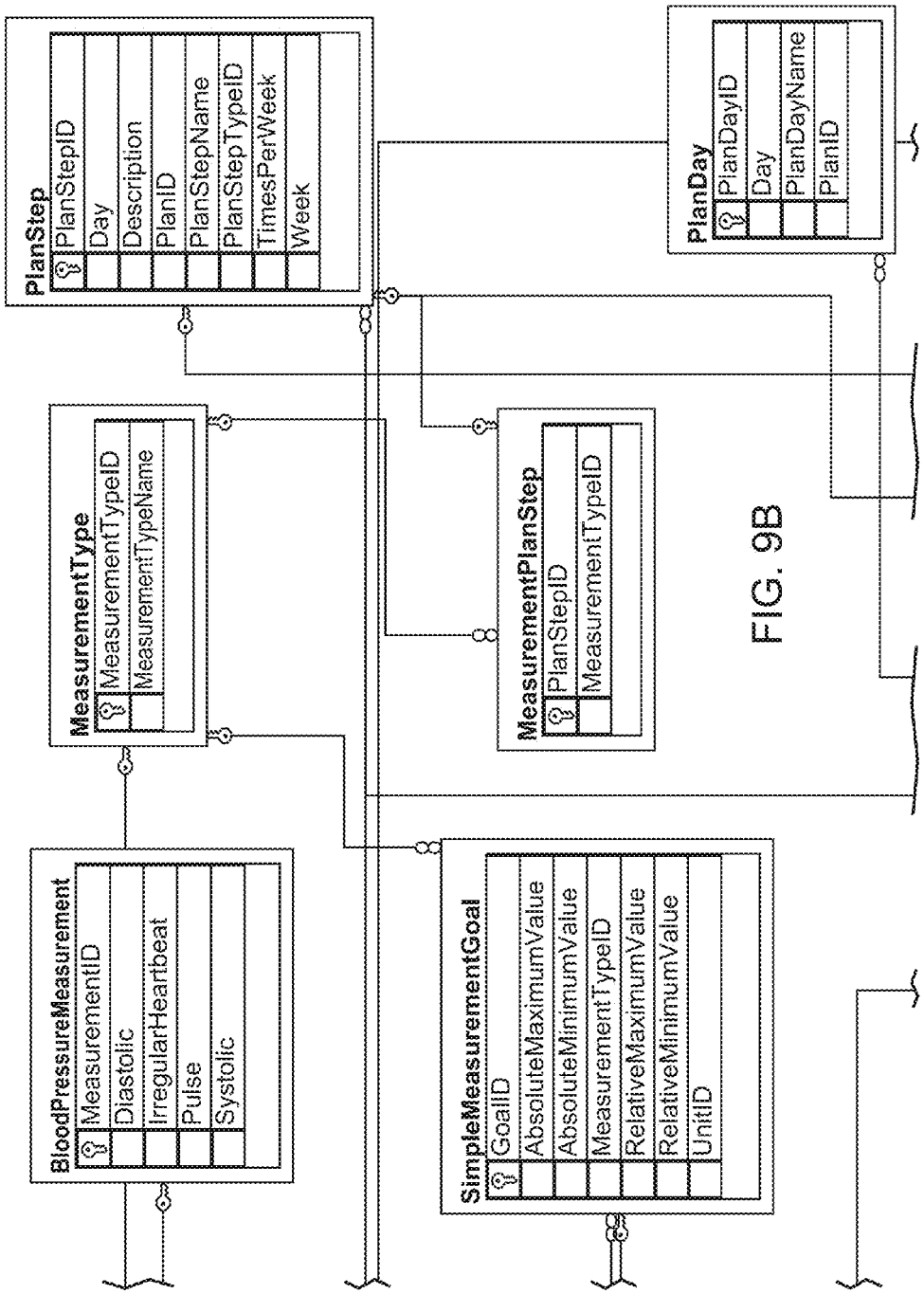
FIGS. 9-13 illustrate the data architecture according to one embodiment.
Figure 9D:
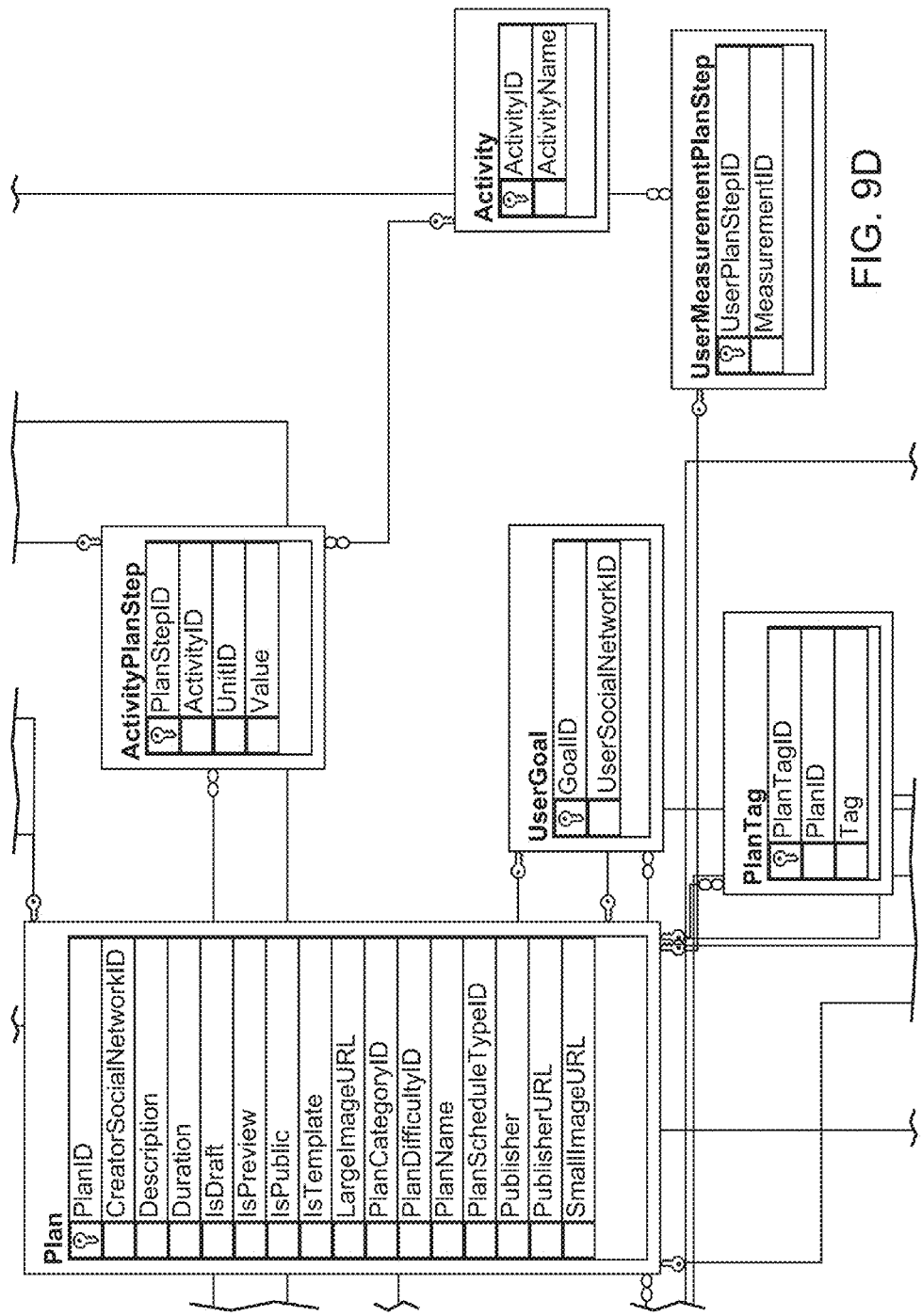
Figure 9F:
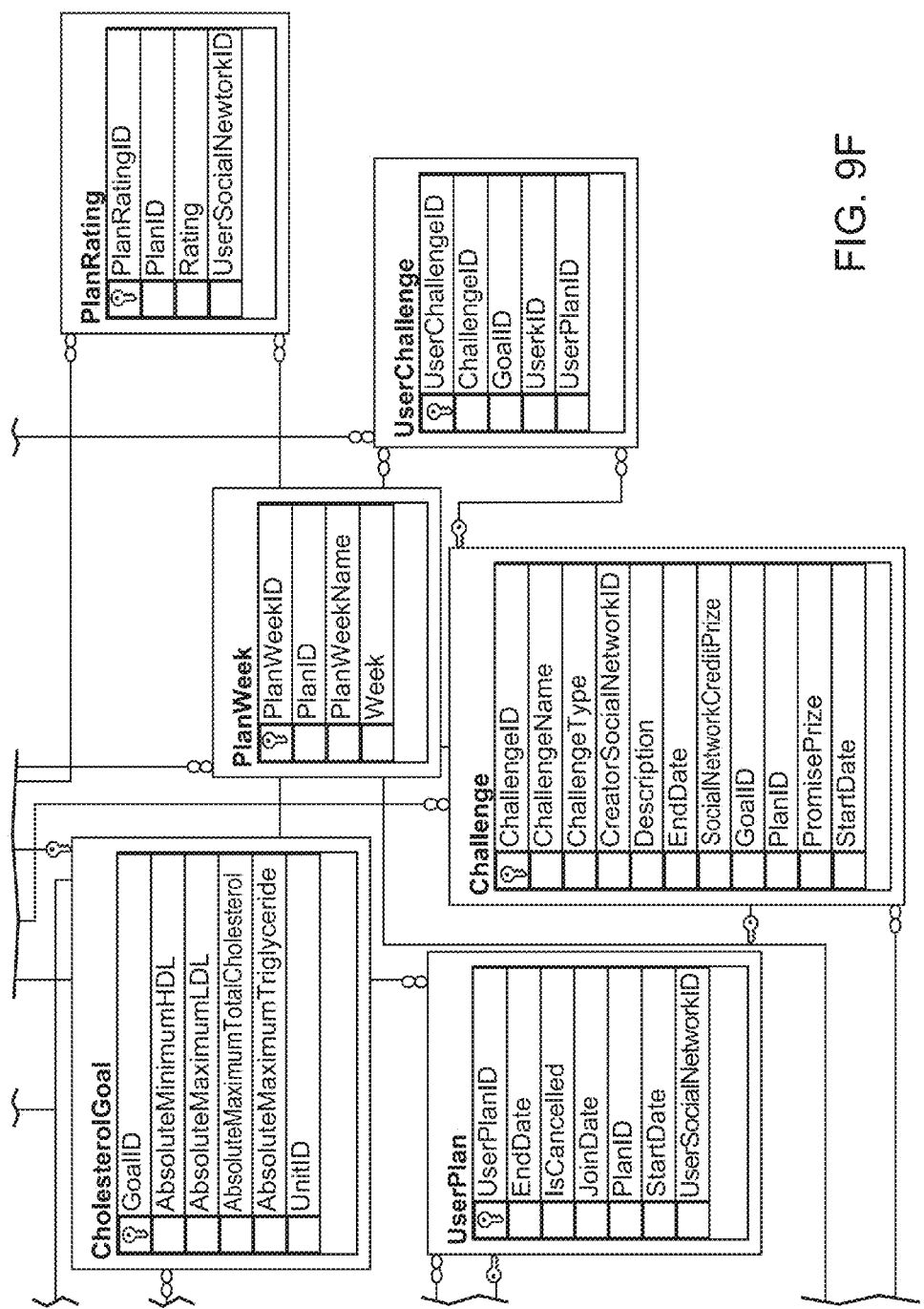

FIG. 9 provides an overview of the interrelationship between all data. It includes records for a user, a routine, a goal, a user's goal, data provided as part of the plan, etc.

Figure 10:
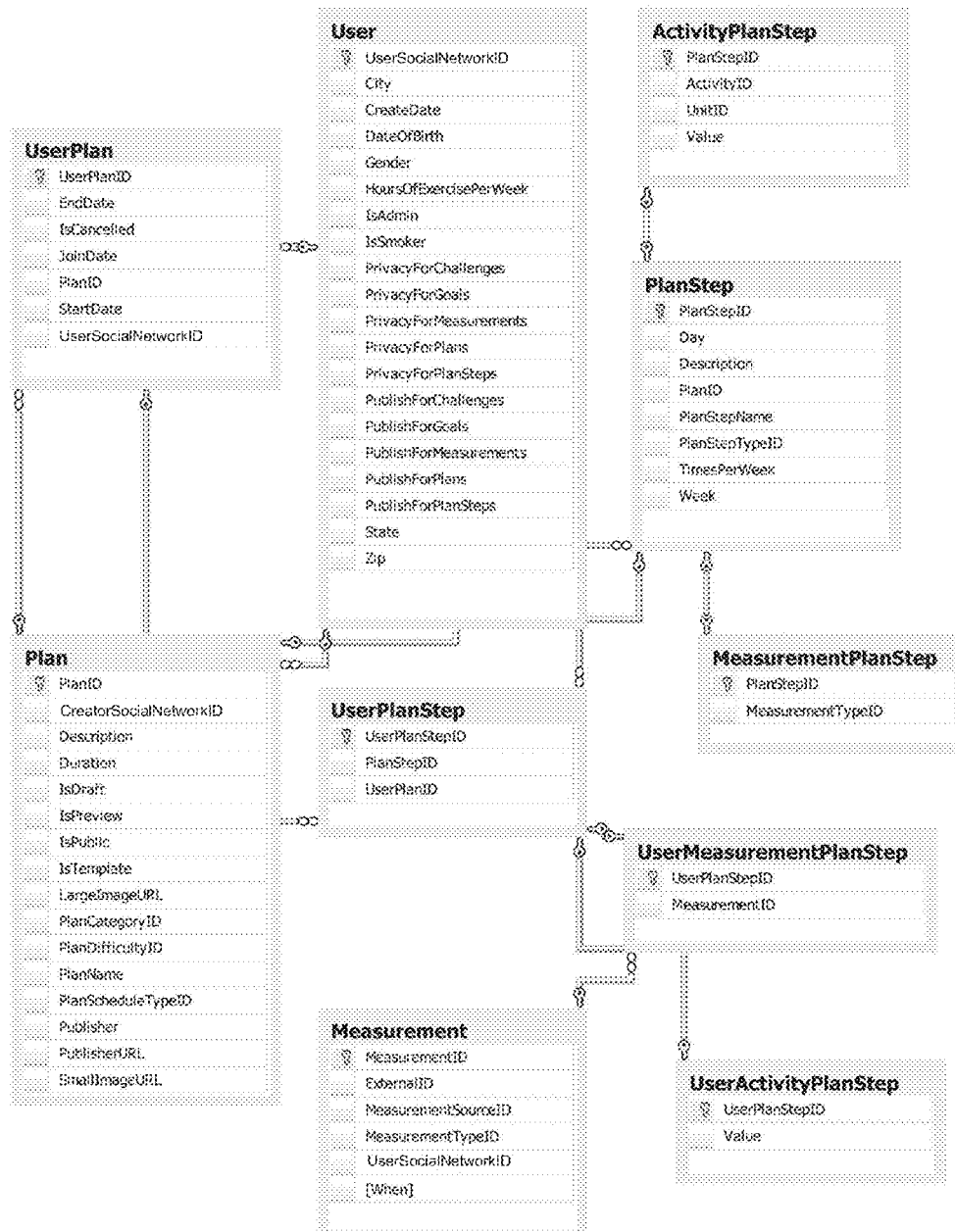

FIG. 10 shows the data for tracking a user's compliance with a routine.

Figure 11:
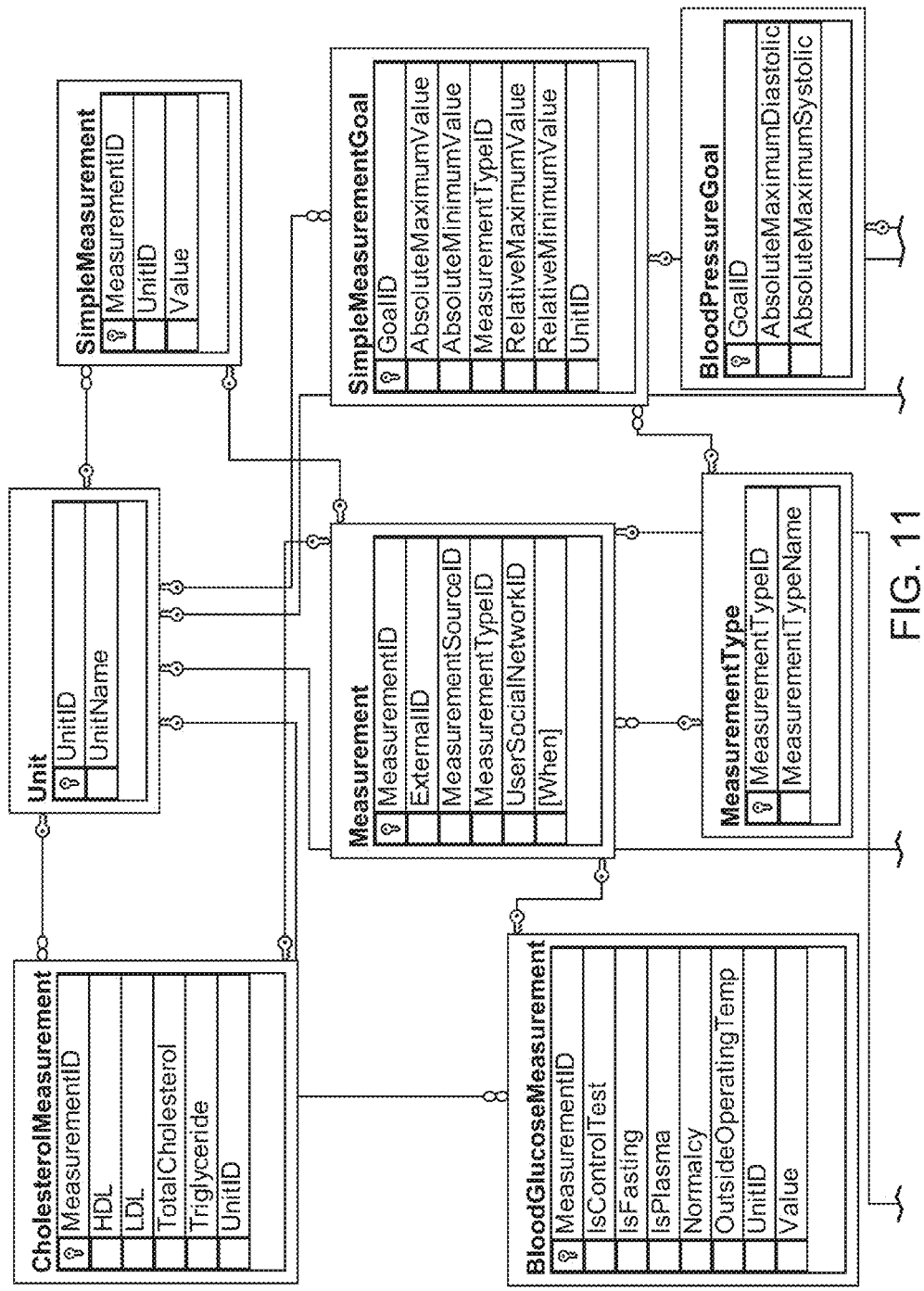
Figure 11:
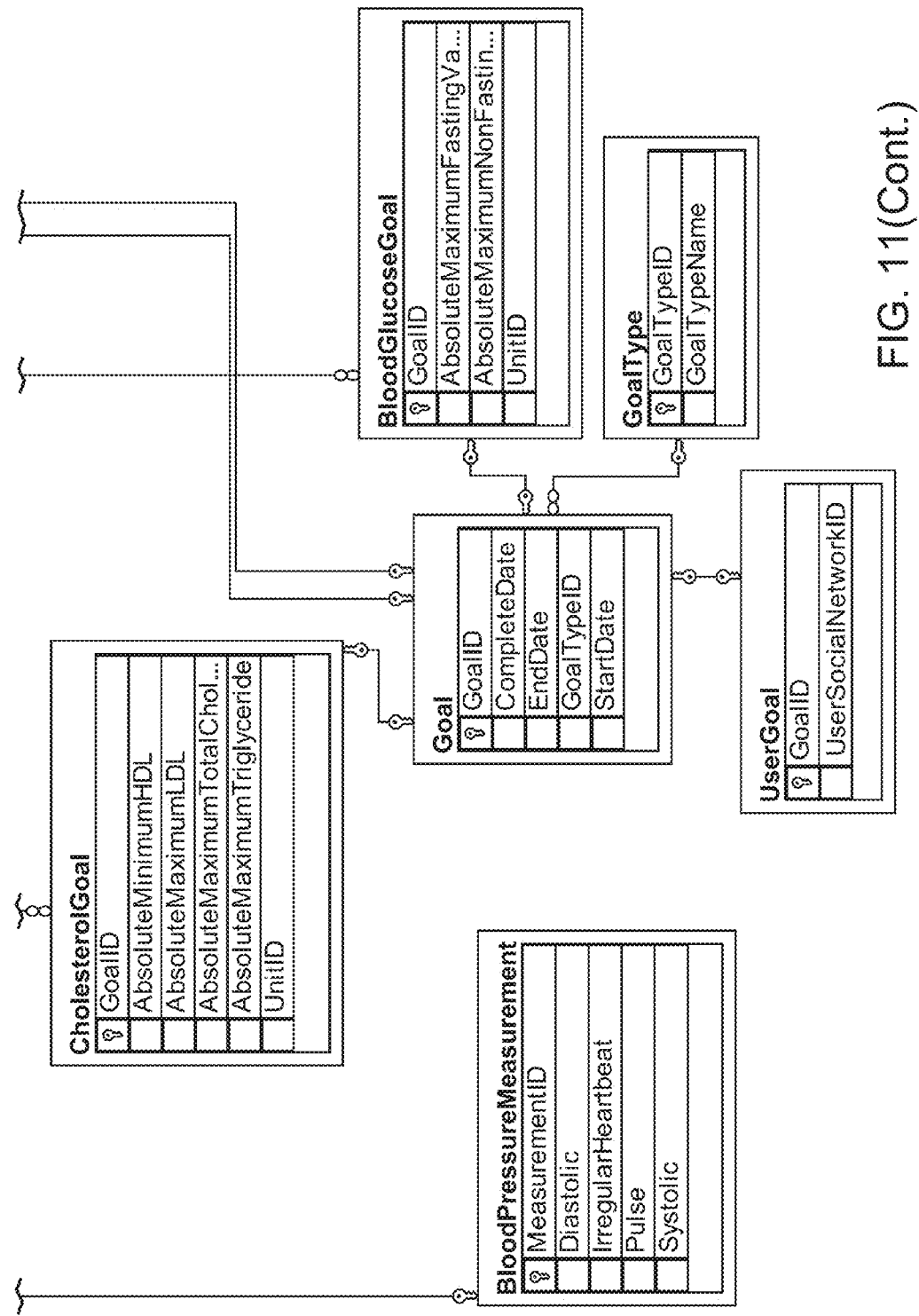

FIG. 11 shows the data for tracking a user's progress towards a goal.

Figure 12:
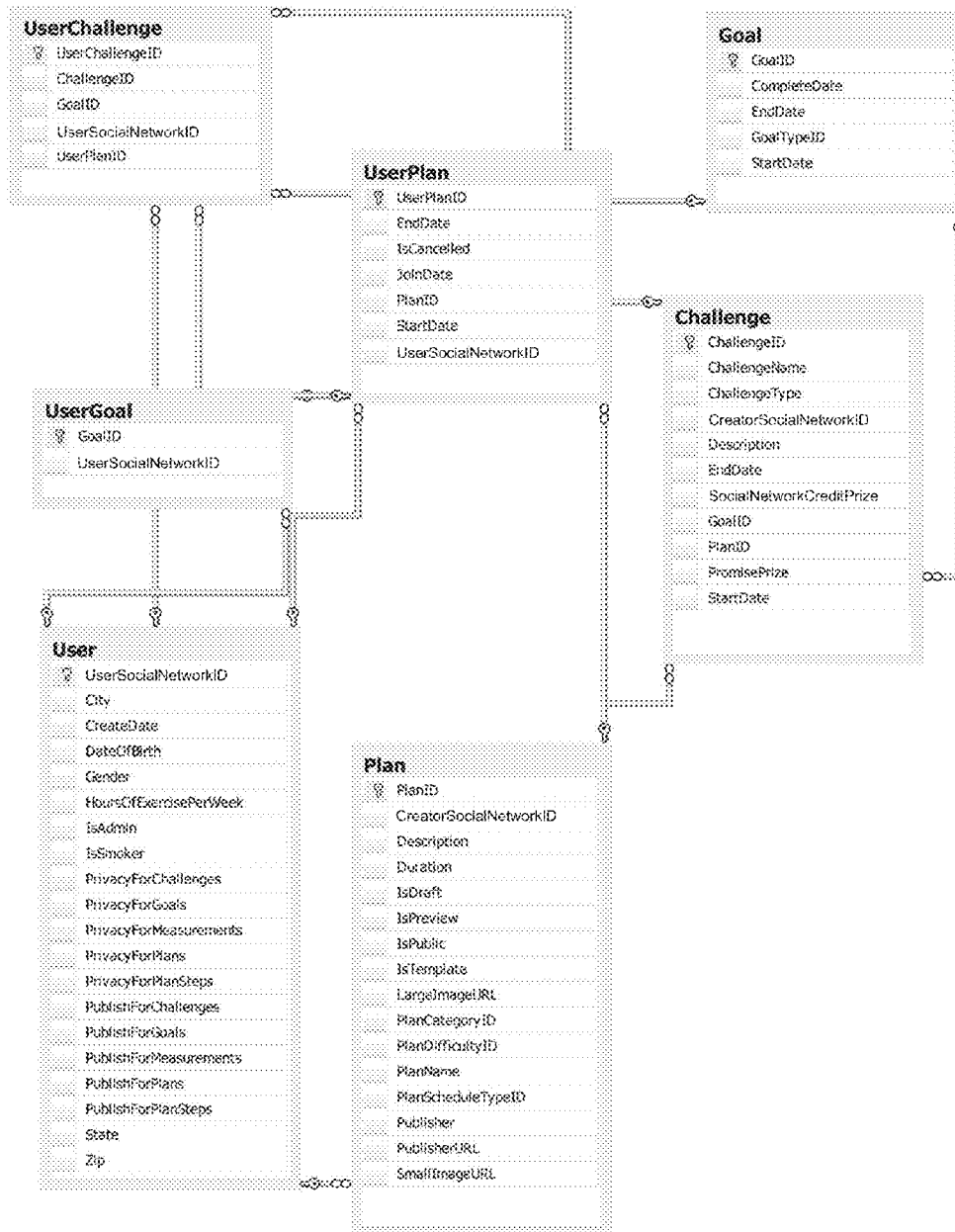

FIG. 12 shows the data in tracking progress for a challenge.

Figure 13:
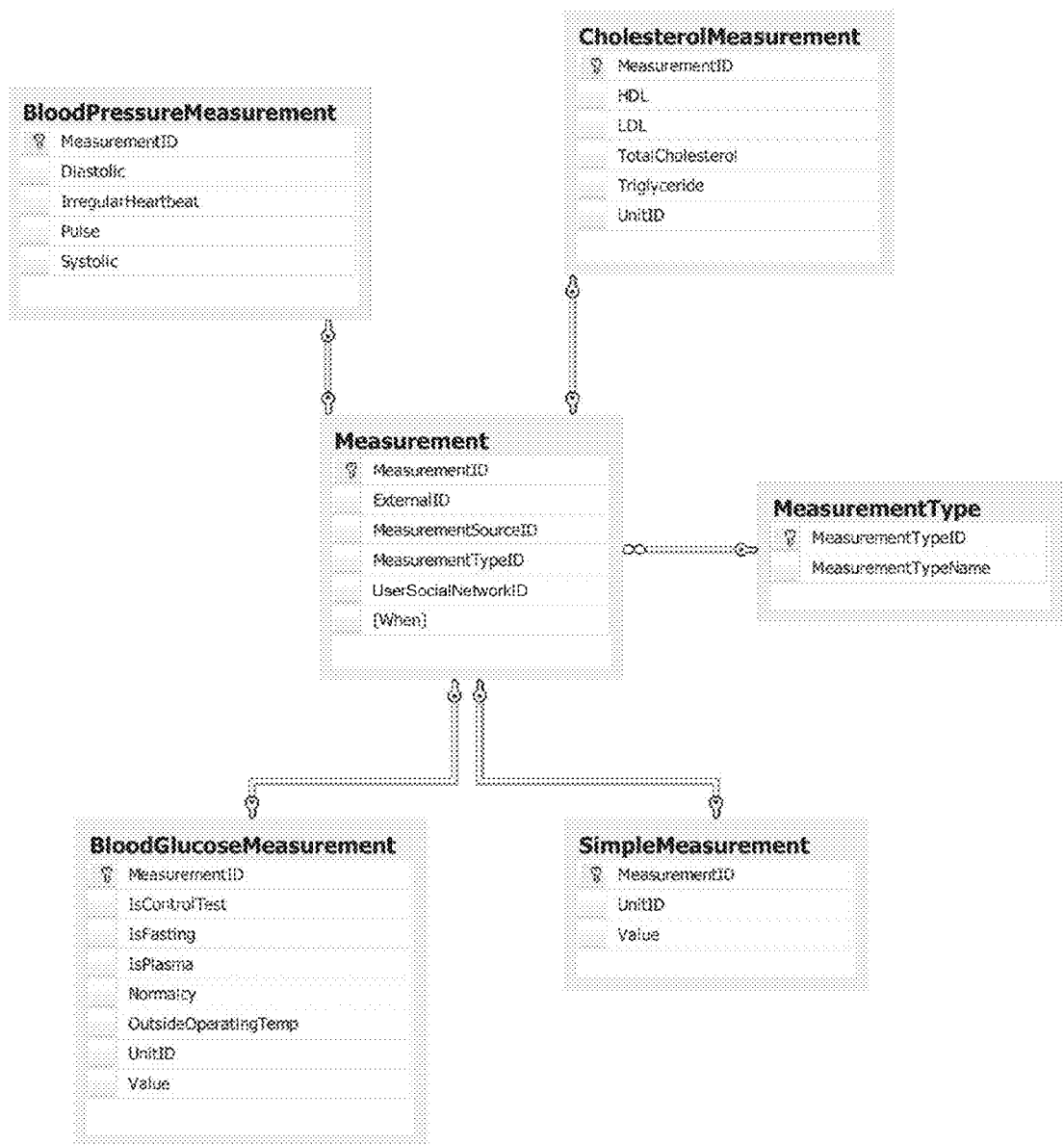

FIG. 13 shows the data included in measurements received from a health monitoring device 170.

In this description, the term "module" refers to computational logic and data for providing the specified functionality. A module can be implemented in hardware, firmware, and/or software. Where the modules described herein are implemented as software, the modules can be implemented as a standalone program, but can also be implemented through other means, for example as part of a larger program, as a plurality of separate programs, or as one or more statically or dynamically linked libraries. In any of these software implementations, the modules (for example plan creation module 110, recommendation module 115, status module 120, publication module 125, challenge module 130 and assessment module 135) are stored on the computer readable persistent storage devices of the system 100, loaded into memory, and executed by the one or more processors of the system's computers.

The particular division of functionality between the various components may differ from that described herein, given the variety of software development environments and hardware platforms that may be used to practice the invention. Thus, the particular functions of the various above describe components may be provided in more or fewer elements. Accordingly, the disclosure of the present invention is intended to be illustrative, but not limiting, of the scope of the invention, which is set forth in the following claims.

It is not necessary for the elements to be organized as shown; the elements can be hosted by other entities or in some cases may even stand-alone. In some implementations of the system, the various elements may also appear in different configurations. Furthermore, it is not necessary for every embodiment of the invention to include all of the elements depicted. Likewise, as other elements and sub-elements are described throughout the invention, it should be understood that various embodiments of the invention may exclude elements and sub-elements described, that the elements and sub-elements may be hosted in configurations other than those shown, and that elements and sub-elements, even within an element, may be hosted in different locations or by different entities than those shown.

The particular naming of the components, capitalization of terms, the attributes, data structures, or any other programming or structural aspect is not mandatory or significant, and the mechanisms that implement the invention or its features may have different names, formats, or protocols.

Some portions of the above description describe the invention in terms of algorithms and symbolic representations of operations on information. These algorithmic descriptions and representations are the means used by those skilled in the data processing arts to most effectively convey the substance of their work to others skilled in the art. These operations, while described functionally, computationally, or logically, are understood to be implemented by computer programs or equivalent electrical circuits, microcode, or the like.

The terms used to describe various quantities, data values, and computations are understood to be associated with the appropriate physical quantities and are merely convenient labels applied to these quantities. Unless specifically stated otherwise as apparent from the discussion, it is appreciated that throughout the description, discussions utilizing terms such as "processing" or "computing" or "calculating" or "determining" or the like, refer to the action and processes of a computer system, or similar electronic computing device, that manipulates and transforms data represented as physical (electronic) quantities within the computer system memories or registers or other such information storage, transmission or display devices.

The invention also relates to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention.

The invention claimed is:

1. A method executed in a computer system for providing and monitoring health-related activities to users, the computer system including a database, the method comprising:

receiving at the computer system a request for health-related programs, the request including at least one criterion;

accessing in the database a profile for the user, the profile comprising health-related information about the user;

automatically selecting from the database a plurality of health-related programs matching the criteria and responsive to the health-related information about the user, each matching health-related program comprising a goal or a routine including at least one task;

transmitting for display to a client device of the user the matching health-related programs;

receiving from the user a selection of one of the matching health-related programs;

storing in the database an identifier for the selected health-related program in association with the user to indicate the user's participation with the health-related program;

receiving data related to the user's progress towards the goal or completion of one of the tasks of the routine in the selected health-related program;

storing the received data in the database in association with the user and the selected health-related program, to update the selected health-related program with the user's progress;

determining a status of the user in the selected health-related program based upon the received data related to the user's progress; and transmitting for display to the client device of the user the status of the user in the selected health-related program.

2. The method of claim 1 wherein receiving data related to the user's progress towards the goal or completion of one of the tasks of the routine in the selected health-related program comprises receiving the data from a health-monitoring device used by the user.

3. The method of claim 1 wherein the received data comprises a numerical measurement.

4. The method of claim 3 wherein determining the status comprises comparing the numerical measurement to a threshold measurement associated with the goal or the routine.

5. The method of claim 1 wherein the received data comprises a plurality of measurements.

6. The method of claim 1 wherein the selected health-related program comprises a routine including at least one task, and wherein receiving data related to the user's progress towards the goal or completion of one of the tasks of the routine in the selected health-related program comprises an indication of the user's completion of one of the tasks of the routine.

7. The method of claim 1 further comprising:

receiving from a client device of a second user a selection of the health-related program;

storing in the database the identifier for the one health-related program as associated with the second user to indicate the second user's participation in the health-related program;

receiving data related to a second progress of the second user in the health-related program;

determining a second status of the second user in the health-related program; and providing both the status and the second status for display to the user and the second user.

8. A computer-implemented system, comprising a processor for executing program code; and a non-transitory computer-readable storage medium storing program code executable to perform steps comprising:

receiving a request for health-related programs, the request including at least one criterion;

accessing a profile for the user, the profile comprising health-related information about the user;
automatically selecting from a database a plurality of health-related programs matching the criteria and responsive to the health-related information about the user, each matching health-related program comprising a goal or a routine including at least one task;
transmitting for display to a client device of the user the matching health-related programs;
receiving from the user a selection of one of the matching health-related programs;
storing in the database an identifier for the selected health-related program in association with the user to indicate the user's participation with the health-related program;
receiving data related to the user's progress towards the goal or completion of one of the tasks of the routine of the selected health-related program;
storing the received data in the database in association with the user and the selected health-related program, to update the selected health-related program with the user's progress;
determining a status of the user in the selected health-related program based upon the received data related to the user's progress; and
transmitting for display to the client device of the user the status of the user in the selected health-related program.

9. The system of claim 8 wherein receiving data related to the user's progress towards the goal or completion of one of the tasks of the routine in the selected health-related program comprises receiving the data from a health-monitoring device used by the user.

10. The system of claim 8 wherein the received data comprises a numerical measurement.

11. The system of claim 10 wherein determining the status comprises comparing the numerical measurement to a threshold measurement associated with the health-related program.

12. The system of claim 8 wherein the received data comprises a plurality of measurements.

13. The system of claim 8 wherein the selected health-related program comprises a routine including at least one task, and wherein receiving data related to the user's progress towards the goal or completion of one of the tasks of the routine of the selected health-related program comprises an indication of the user's completion of one of the tasks of the routine.

14. The system of claim 8 further comprising program code executable to perform steps comprising:
receiving from a client device of a second user a selection of the health-related program;
storing in the database the identifier for the one health-related program as associated with the second user to indicate the second user's participation in the health-related program;
receiving data related to a second progress of the second user in the one health-related program;
determining a second status of the second user in the one health-related program; and
providing both the status and the second status for display to the user and the second user.

15. A non-transitory computer-readable storage medium containing program code, comprising program code that when executed by a processor performs the steps of:
receiving a request for health-related programs, the request including at least one criterion;
accessing a profile for the user, the profile comprising health-related information about the user;
automatically selecting from a database a plurality of health-related programs matching the criteria and responsive to the health-related information about the user, each matching health-related program comprising a goal or a routine including at least one task;
transmitting for display to a client device of the user the matching health-related programs;
receiving from the user a selection of one of the matching health-related programs;
storing in the database an identifier for the selected health-related program in association with the user to indicate the user's participation with the health-related program;
receiving data related to the user's progress towards the goal or completion of one of the tasks of the routine of the selected health-related program;
storing the received data in the database in association with the user and the selected health-related program, to update the selected health-related program with the user's progress;
determining a status of the user in the selected health-related program based upon the received data related to the user's progress; and
transmitting for display to the client device of the user the status of the user in the selected health-related program.

16. The computer-readable storage medium of claim 15 wherein receiving data related to the user's progress towards the goal or completion of one of the tasks of the routine in the selected health-related program comprises receiving the data from a health-monitoring device used by the user.

17. The computer-readable storage medium of claim 15 wherein the received data comprises a numerical measurement.

18. The computer-readable storage medium of claim 17 wherein determining the status comprises comparing the numerical measurement to a threshold measurement associated with the health-related program.

19. The computer-readable storage medium of claim 15 wherein the received data comprises a plurality of measurements.

20. The computer-readable storage medium of claim 15 wherein the selected health-related program comprises a routine including at least one task, and wherein receiving data related to the user's progress towards the goal or completion of one of the tasks of the routine of in the selected health-related program comprises an indication of the user's completion of one of the tasks of the routine.

21. The computer-readable storage medium of claim 15 further comprising program code for:
receiving from a client device of a second user a selection of the health-related program;
storing in the database the identifier for the one health-related program as associated with the second user to indicate the second user's participation in the health-related program;
receiving data related to a second progress of the second user in the one health-related program;
determining a second status of the second user in the one health-related program; and
providing both the status and the second status for display to the user and the second user.

* * * * *